US009539104B2

(12) United States Patent
Horton et al.

(10) Patent No.: US 9,539,104 B2
(45) Date of Patent: *Jan. 10, 2017

(54) OSTEOCONDUCTIVE IMPLANTS AND METHODS OF USING SAME (71) Applicant: NuTech Spine, Inc., Birmingham, AL (US)

(72) Inventors: Kenneth L. Horton, Birmingham, AL (US); Gregory J. Yager, Mount Olive, AL (US); Howard P. Walthall, Jr., Birmingham, AL (US)

(73) Assignee: NuTech Spine, Inc., Birmingham, AL (US)

( * ) Notice: Subject to any disclaimer, the term of this patent is extended or adjusted under 35 U.S.C. 154(b) by 260 days.

This patent is subject to a terminal disclaimer.

(21) Appl. No.: 13/750,212

(22) Filed: Jan. 25, 2013

(65) Prior Publication Data

US 2013/0144386 A1    Jun. 6, 2013

Related U.S. Application Data

(63) Continuation-in-part of application No. 13/250,096, filed on Sep. 30, 2011, now abandoned.

(51) Int. Cl.
*A61F 2/28* (2006.01)
*A61L 27/36* (2006.01)
(Continued)

(52) U.S. Cl.
CPC .......... *A61F 2/4455* (2013.01); *A61B 17/707* (2013.01); *A61K 35/50* (2013.01); *A61L 27/3604* (2013.01);
(Continued)

(58) Field of Classification Search
CPC .............................. A61F 2/4455; A61K 35/50
(Continued)

(56) References Cited

U.S. PATENT DOCUMENTS 3,472,228 A * 10/1969 Tanner, Jr. .................... 606/132
4,599,084 A *  7/1986 Nashef ......................... 128/898
(Continued)

FOREIGN PATENT DOCUMENTS

WO    WO 2009044408 A1 *  4/2009
WO    WO 2010012025 A1 *  2/2010

OTHER PUBLICATIONS

Chalmers et al. (The Journal of Bone and Joint Surgery, vol. 57-B, No. 1, 1975).*

(Continued)

*Primary Examiner* — Allison Fox
(74) *Attorney, Agent, or Firm* — Maynard, Cooper and Gale, P.C.; C. Brandon Browning (57) ABSTRACT

Implants for promoting bone growth and methods of using same, the implants including a perforated placental membrane sheet wrapped around an osteoconductive material composed of bone chips, bone granules, bone powders or combinations thereof, the osteoconductive material being configured for providing a scaffold upon which bone growth can occur. The placental membrane sheet acts to maintain the osteoconductive material in a cohesive, organized configuration within a site of a patient where bone growth is to be induced. The perforations in the placental membrane sheet create passageways in the exterior of the implant through which the osteoconductive material can communicate with adjacent bone surfaces which are to be fused.

31 Claims, 5 Drawing Sheets

(51) Int. Cl.
    *A61K 35/32*     (2015.01)
    *A61K 35/50*     (2015.01)
    *A61F 2/44*      (2006.01)
    *A61L 27/50*     (2006.01)
    *A61B 17/70*     (2006.01)

(52) U.S. Cl.
    CPC ........ *A61L 27/3608* (2013.01); *A61L 27/3645* (2013.01); *A61L 27/50* (2013.01); *A61L 2430/02* (2013.01); *A61L 2430/38* (2013.01)

(58) Field of Classification Search
    USPC ..................................................... 623/17.11
    See application file for complete search history.

(56) References Cited

U.S. PATENT DOCUMENTS

| | | | | |
|---|---|---|---|---|
| 4,674,488 | A * | 6/1987 | Nashef ................. | A61L 31/005 606/76 |
| 5,676,699 | A * | 10/1997 | Gogolewski .......... | A61F 2/2846 623/16.11 |
| 8,883,210 | B1 * | 11/2014 | Truncale et al. ............. | 424/484 |
| 2005/0107876 | A1 * | 5/2005 | Kim et al. ................. | 623/15.12 |

OTHER PUBLICATIONS

Friedenstein et al. (Clinical Orthopaedics & Related Research, vol. 59, p. 21-38, 1968).*
Wlodarski et al. (Calcified Tissue Research, vol. 5, p. 70-79, 1970).*
Fogh et al. (Experimental Biology and Medicine, vol. 94, No. 3, p. 532-537, 1957).*
Kothiwale et al. (Cell and Tissue Banking, vol. 10, p. 317-326, 2009).*

* cited by examiner

OSTEOCONDUCTIVE IMPLANTS AND METHODS OF USING SAME

RELATED REFERENCES

This application is a continuation in part of and claims priority to U.S. patent application Ser. No. 13/250,096, filed Sep. 30, 2011, and titled, "Expandable Placental Membrane and Methods of Making and Storing Same," the entire contents of which are incorporated herein by reference.

FIELD OF THE INVENTION

The present invention is directed to implants for promoting bone growth. More particularly, the present invention is directed to a surgical implant and method of using same, the implant including an osteoconductive material wrapped in a placental membrane sheet.

BACKGROUND OF THE INVENTION

A variety of therapeutic treatments are available for inducing bone growth at a desired site in a patient. Examples of such therapeutic treatments exist in the field of spinal surgery, including a variety of spinal fusion procedures. Illustratively, in posterolateral fusion procedures, bone growth is induced to fuse transverse processes of adjacent vertebrae, typically in the lumbar spine. In posterolateral fusion, the surgical approach to the spine is from the back, often through a midline incision. A bone graft harvested from the iliac crest of other donor zones of the patient is laid out in the posterolateral portion of the spine. Alternatively, allograft or synthetic bone graft material may be used. The back muscles that attach to the transverse processes are elevated to create a bed upon which to lay the bone graft. The back muscles are then laid back over the bone graft, creating tension to hold the bone graft in place.

A shortcoming of present posterolateral spinal fusion methods is the reliance on muscle tension or other inadequate means for maintaining bone grafts in place between transverse processes. This is especially so when the bone graft is presented as bone chips, granules or powders which can migrate out of the posterolateral portion of the spine over time. The present invention addresses the problem of bone graft containment and undesired bone graft migration from sites in a patient where bone growth is desired.

SUMMARY OF THE INVENTION

The present invention is directed to implants for promoting bone growth and methods of using same. The implants generally include an osteoconductive material and a perforated placental membrane sheet wrapped around the osteoconductive material. The placental membrane sheet acts to maintain the osteoconductive material in a cohesive, organized configuration within a site of a patient where bone growth is to be induced. The perforations in the placental membrane sheet create passageways in the exterior of the implant through which the osteoconductive material can communicate with adjacent bone surfaces which are to be fused together, in order to encourage such fusion.

According to one aspect of the invention, there is provided a surgical implant including an osteoconductive material in contact with a perforated placental membrane sheet. The osteoconductive material is selected from a group consisting of bone, bone chips, demineralized bone powder, cancellous bone, cortical bone, synthetic bone substitutes containing calcium phosphate or hydroxyapatite, and combinations thereof. Bone morphogenetic proteins or other growth factors can be included in the implant to increase the rate of bone growth. Preferably, the placental membrane sheet is wrapped around the osteoconductive material so that the osteoconductive material is arranged entirely within an interior void defined by the placental membrane sheet. This is accomplished by rolling the placental membrane sheet to form an elongate implantable structure containing the osteoconductive material and/or folding the placental membrane over the osteoconductive material. The resulting elongate structure is configured to have a length, thickness and width necessary for affecting the desired bone to bone fusion. In the case of posterolateral spinal fusions, the elongate structure has may have a length of up to about 6 centimeters or more, which is adequate to provide an implant that extends to and between adjacent transverse processes. Given an implant length of about 6 centimeters, it is anticipated that about 5 cubic centimeters of the osteoconductive material is required to fuse adjacent transverse processes.

According to another aspect of the invention, there is provided an elongate surgical implant including a perforated placental membrane sheet wrapped around an osteoconductive material selected from a group consisting of bone, bone chips, demineralized bone powder, cancellous bone, cortical bone, synthetic bone substitutes, and combinations thereof. The perforations are in the form of slits and form a predetermined pattern in the placental membrane sheet. Preferably, the implant has an exterior surface displaying an epithelial cell layer which is accomplished by facing an amnion layer of the placenta membrane sheet outwardly. The outwardly facing epithelial cell layer serves to impede adherence of the implant to a patient's muscle or other surrounding tissue when the implant is inserted into a region where bone growth is to be induced.

According to another aspect of the invention, there is provided a method a making a surgical implant including contacting an osteoconductive material with a perforated placental membrane sheet and forming an elongate structure from the perforated placental membrane sheet, the elongate structure having an exterior surface and an interior containing the osteoconductive material. The osteoconductive material is arranged within the interior by wrapping the placental membrane sheet around the osteoconductive material and/or folding the osteoconductive material within the placental membrane sheet. Alternatively, the osteoconductive bone material can be placed on top of the placental membrane sheet in vivo, followed by folding the placental membrane sheet over the osteoconductive material. Additionally, the osteoconductive material can be placed between adjacent bone surfaces in vivo, followed by placing placental membrane sheet on top of the osteoconductive material.

According to another aspect of the invention, there is provided a method for inducing bone growth in a patient including inserting an implant into a patient at a site so as to induce bone growth wherein the implant includes an osteoconductive material in contact with a perforated placental membrane sheet. The site can be in a spine, a long bone or a cranial defect of the patient. Pursuant to this method, the implant is contacted to a first bone surface and a second bone surface of the patient thereby forming a bridge between the bone surfaces and path along which bone growth can occur.

According to another aspect of the invention, there is provided a method for inducing bone growth in a patient including wrapping a perforated placental membrane sheet around an osteoconductive material to form an implant, inserting the implant into a patient at a site so as to induce bone growth and contacting the implant to a first bone surface and a second bone surface of the patient. Preferably, the implant is arranged to display an epithelial cell layer on the exterior surface of the implant for suppressing adhesion of the placental membrane sheet to surrounding tissue such as muscle, tendons, ligaments and the like.

According to yet another aspect of the invention, there is provided a method for inducing bone growth in a patient including perforating a placental membrane sheet and placing an osteoconductive material and the placental membrane sheet into a patient at a site so as to induce bone growth. Placement of the placental membrane sheet and osteoconductive material can occur one or several ways. For example, the placental membrane sheet can be placed at the site after the osteoconductive material is inserted into the patient. In this instance, the placental membrane sheet can be arranged on top of the osteoconductive material thereby suppressing the upward and lateral migration of the material out of the site. Alternatively, the placental membrane sheet can placed at the site before the osteoconductive material is inserted. In this instance, the osteoconductive material is placed on top of the placental membrane sheet in a substantially linear fashion. Thereafter, the sheet is folded over the osteoconductive material thereby encapsulating the material within the sheet. In this manner, the outward or radial migration of the osteoconductive material from implant is restrained or altogether prevented.

A further understanding of the nature and advantages of the present invention will be realized by reference to the remaining portions of the specification and the drawings.

DETAILED DESCRIPTION OF THE INVENTION

The present invention is directed to osteoconductive implants that include an osteoconductive material having a surface covered at least in part by a placental membrane sheet. The osteoconductive material can be provided as a particulate material, including either powder form, or larger particulate materials such as granules or chips. The particulate osteoconductive material is effective in providing a scaffold for bone growth. The osteoconductive material may for example be bone, especially cortical bone or cancellous bone. The osteoconductive material may also be a synthetic bone substitute, many formulations of which are well known in the art. The implants include a sufficient amount of osteoconductive material to provide a scaffold effective to remain in the patient for a period of time adequate for the formation of osteoid in the void for which bone growth is desired. To further promote bone growth, growth factors or other bone growth promoting proteins may be added to the osteoconductive material.

The placental membrane sheet of the present invention is produced from placentas collected from consenting donors in accordance with the Current Good Tissue Practice guidelines promulgated by the U.S. Food and Drug Administration. Soon after the birth of a human infant via a Cesarean section delivery, the intact placenta is retrieved, and the placental membrane is dissected from the placenta. Afterwards, the placental membrane is cleaned of residual blood, placed in a bath of sterile solution, stored on ice and shipped for processing. Once received by the processor, the placental membrane is rinsed to remove any remaining blood clots, and if desired, rinsed further in an antibiotic rinse. The placental membrane is then stored in packs containing a sterile solution or freeze dried. The processes for harvesting placental membranes and making a perforated, expandable placental membrane sheet therefrom are described in co-pending U.S. patent application Ser. No. 13/250,096.

Figure 1:
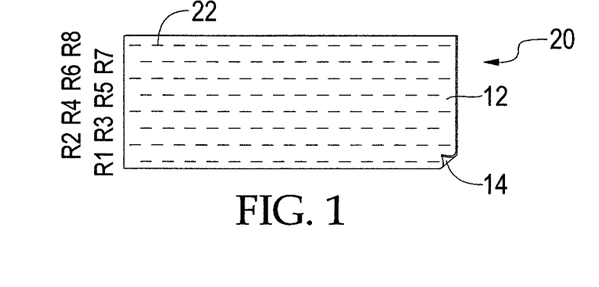
FIG. 1 is a top plan view of a perforated placental membrane sheet in accordance with a preferred embodiment of the present invention.
Figure 2:
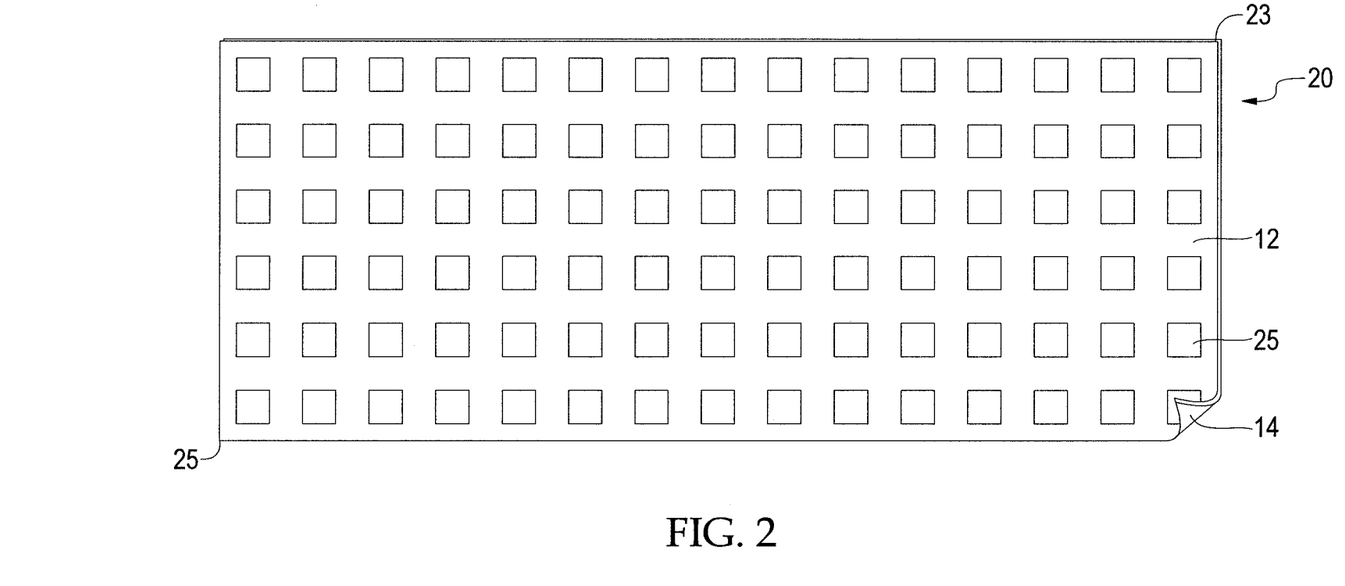
FIG. 2 is a top plan view of the perforated placental membrane sheet of FIG. 2 in an expanded state.

FIGS. 1 and 2 depict an expandable, porous placental membrane sheet 20 in accordance with a preferred embodiment of the invention. Placental membrane sheet 20 is prepared by cutting a placental membrane that has been processed in accordance with the aforementioned procedure into a sheet having desired dimensions. The sheet is then perforated to include a plurality of openings through the placental membrane thereby imparting to the sheet a mesh-like pattern. The resulting expandable, porous placental membrane sheet 20 enables stretching along the length and width of the sheet which, in turn, increases the sizes of the plurality of openings.

Referring to FIG. 1, placental membrane sheet 20 includes a plurality of elongated slits 22 which in combination provide sheet 20 with a mesh-like appearance. Slits 22 extend between and through the amnion layer and the chorion layer of the placental membrane and are formed by processing a placental membrane with a mesher, for example, as described in U.S. Pat. Nos. 6,063,094; 5,004,468; 3,640,279; 3,472,228 and 3,358,688. Depending on the mesher settings, and more particularly, the arrangement and number of the cutting portions of the mesher, slits 22 can vary in size, density and orientation. Further, the slits may be configured to provide openings of varying shapes such as round, square, rectangular and diamond-shaped openings. By varying slit 22 sizes, densities and orientation, the capacity for placental membrane material 20 to expand can be controlled. Preferably, slits 22 are arranged in a series of substantially parallel rows R1 through R8 that extend longitudinally along the length of the sheet 20 with adjacent slits 22 being staggered or offset and slits 22 of alternate rows R1, R3, R5 and R7 and alternate rows R2, R4, R6 and R8 being aligned. Using a mesher, as opposed to forming slits 22 by hand, provides a high through-put method of manufacturing placental membrane sheet 20.

Arranged as described above, slits 22 provide within placental membrane sheet 20 a mesh-like arrangement, the mesh-like arrangement imparting to placental membrane sheet 20 an increased capacity to expand, mostly along the width of sheet 20. For example, referring to FIG. 2, upon applying outward force to placental membrane sheet 20, for example, by grasping two opposing corners 23, 25 of sheet 20 with forceps and pulling placental membrane sheet 20 outwardly, the distance between the edges of the slits 22 moves apart to expand the width of sheet 20. As the sheet expands, slits 22 of placental membrane sheet 20 widen due to lateral and/or vertical movement of slit edges relative to one another, thus expanding slits 22 created by the mesher into openings 25. In this manner, the sizes of the openings can be increased.

Preferably, slits 22 are dispersed over the entire surface of sheet 20 in order to maximize expandability of the material; however, is anticipated that there may be applications where expandability or porosity of sheet 20 may be desired for only certain portions of the material. In those instances, slits 22 may be provided in only a fraction of the material or limited only to certain areas of the material such as around the perimeter of the material, in a central portion of the material, or within a top, bottom, left or right half of the material. For posterolateral spinal fusion applications, it is anticipated that slits 22 will be formed only at the ends of the placental membrane sheet 20 that will contact bone surfaces of the transverse processes, while the central section of sheet 20 remains essentially impermeable or non-porous.

As indicated above, the osteoconductive implants of the invention can include a growth-promoting protein. The protein can be dispersed in the osteoconductive material or applied directly to placental membrane sheet 20. For example, the protein can be a bone morphogenic protein (BMP). Recombinant human BMPs can be used, and may be commercially obtained or prepared as described and known in the art, e.g. in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; and WO94/26892 to Celeste et al. The protein may be isolated from tissue sources such as bone. Methods for isolating BMP from bone are described, for example, in U.S. Pat. No. 4,294,753 to Urist and Urist et al., PNAS 371, 1984. Other therapeutic growth factors may also be used in accordance with the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-$\alpha$ and TGF-$\beta$.

Figure 3:
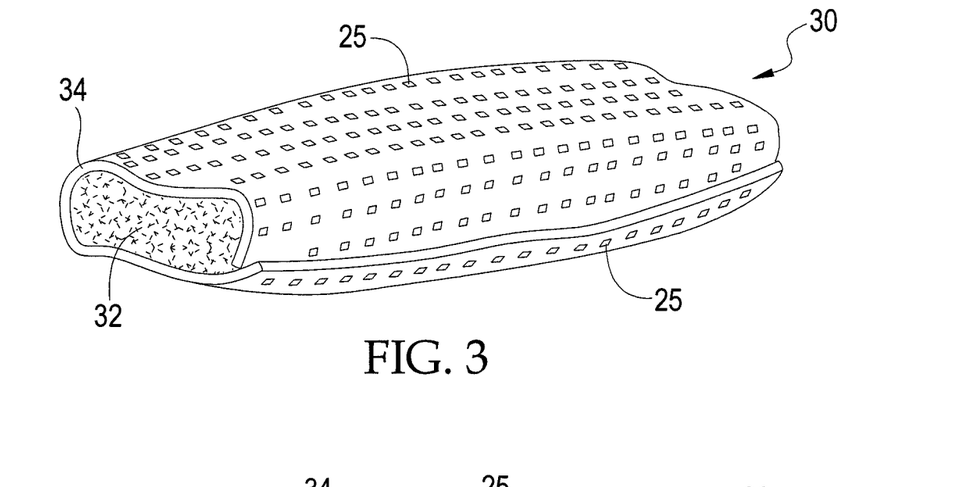
FIG. 3 is a perspective view of an implant in accordance with a preferred embodiment of the invention.
Figure 4:
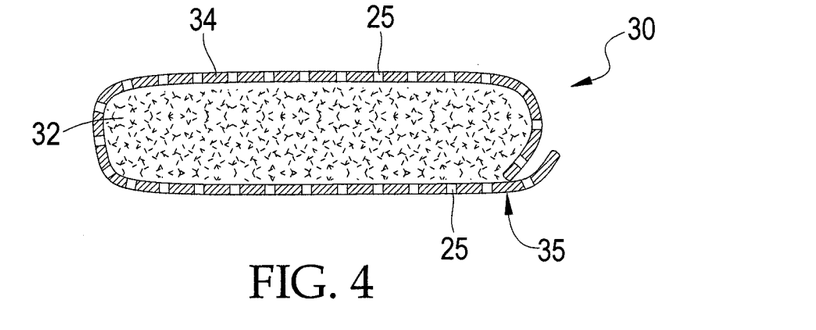
FIG. 4 is a sectional view of the implant of FIG. 3.

Referring now to FIGS. 3 and 4, an illustrative osteoconductive implant 30 of the invention is described. Implant 30 includes an osteoconductive material 32 forming an implant body for occupying a three-dimensional volume through which bone growth is desired. Osteoconductive material 32 can, for example, have a length of about 1 cm to about 10 cm, a width of about 0.5 cm to about 2 cm and a thickness of about 0.5 cm to about 1.5 cm. A perforated placental membrane sheet 34 is used to cover and contain at least a portion of the outer surface of osteoconductive material 32 and can in certain embodiments completely encase and cover all surfaces of osteoconductive material 32. As illustrated in FIGS. 3 and 4, placental membrane sheet 34 is wrapped entirely around osteoconductive material 32 to form an osteoconductive implant of the present invention. Placental membrane sheet 34 can have suitable dimensions for this purpose, for example having a length of about 1 cm to about 10 cm and a width of about 1 cm to about 10 cm. Unless stated otherwise, the dimensions given herein for osteoconductive material 32 and placental membrane sheet 34 are their dimensions when wet (saturated).

Osteoconductive material 32 may comprise bone such as cortical bone or cancellous bone, or synthetic bone substitutes, and be provided as chips, granules, powder or putty. Placental membrane sheet 34 is shown wrapped around osteoconductive material 32 forming an interface 35 therebetween. In this illustrated embodiment, placental membrane sheet 34 wraps completely around osteoconductive material 32 and contacts itself at interface 35. Alternatively, referring to FIG. 5, placental membrane sheet 34 can be folded over osteoconductive material 32 to provide an implant 40 which contacts itself at an interface 41. In accordance with aspects of the present invention, placental membrane sheet 34 and/or osteoconductive material 32 can be impregnated with a liquid carrier including an osteoconductive protein such as a BMP.

Figure 5:
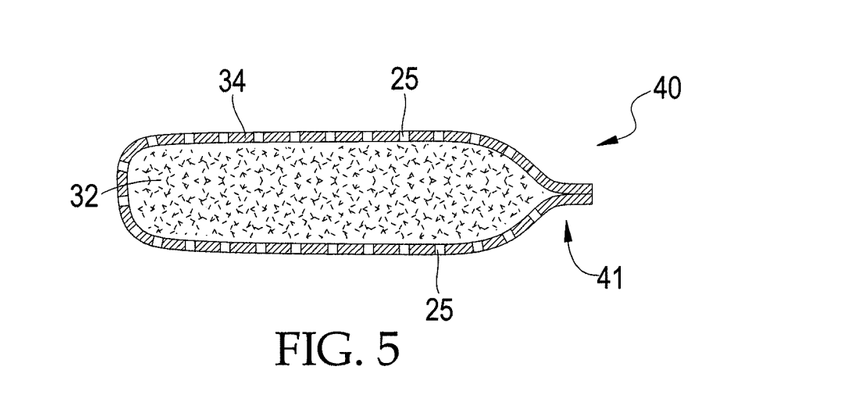
FIG. 5 is a sectional view of an implant in accordance with a preferred embodiment of the present invention formed by folding a perforated placental membrane sheet over an osteoconductive material.

The dimensions of implants 30 and 40 formed from osteoconductive material 32 and placental membrane sheet 34 may vary depending on the application. For posterolateral spinal fusion in humans, the implant dimensions are about 3 cm to about 6 cm in length, about 3 to about 7 cm in width and about 0.2 cm to about 0.5 cm in thickness. The total volume of osteoconductive material 32 for human posterolateral fusion implants should be sufficient to provide the desired fusion mass (e.g. including one level or two level fusions), and may for example range from about 5 cubic centimeters (cc's) to about 20 cc's when the implant materials are wet (saturated).

Figure 6:
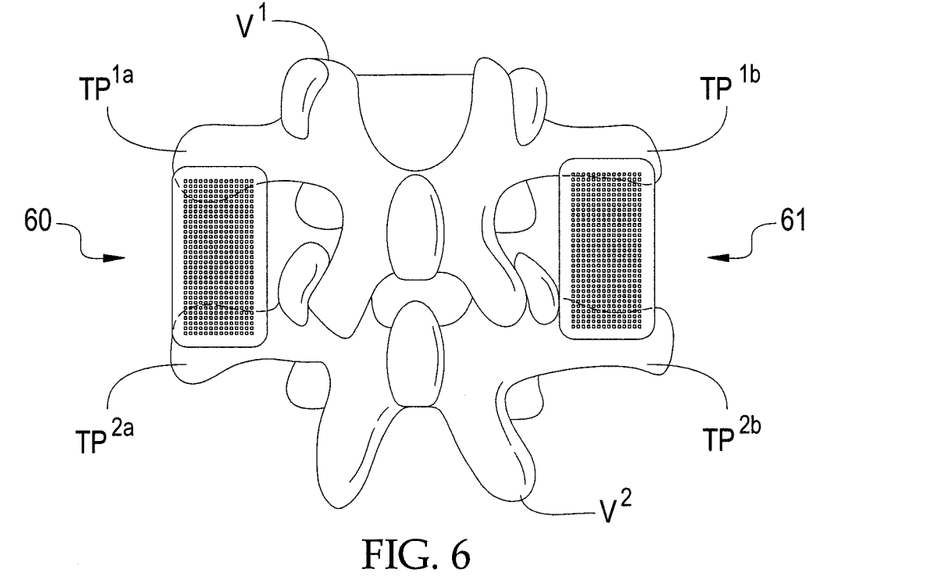
FIG. 6 is a top plan view of the implant of FIG. 4 configured for posterolateral fusion and received between first and second transverse processes of a human patient.

Referring now to FIG. 6, shown are two osteoconductive implants 60 and 61 of the invention in a schematic representation wherein they can facilitate posterolateral fusion in a human patient. A bilateral fusion is shown between a first vertebra $V^1$ and a second vertebra $V^2$. In such a procedure, a first osteoconductive implant 60 traverses the space between a transverse process $TP^{1a}$ of $V^1$ and transverse process $TP^{2a}$ of $V^2$. A similar arrangement is shown on the opposite side wherein an implant 61 contacts transverse process $TP^{1b}$ of the $V^1$ and transverse process $TP^{2b}$ of vertebrae $V^2$ and traverses the space therebetween. Osteoconductive implants 60, 61 thereby induce bone growth from the surfaces of the contacted transverse processes, which bone growth effectively extends through the volume occupied by the osteoconductive implants 60,61 resulting in arthrodesis of the transverse processes and fusion of vertebrae $V^1$ with vertebrae $V^2$. If desired, for such procedures the surfaces of the involved transverse processes may be decorticated to facilitate the fusion process. Techniques and implements for decortication are well known to those of ordinary skill in the art and can be used within the scope of the invention.

Figure 7:
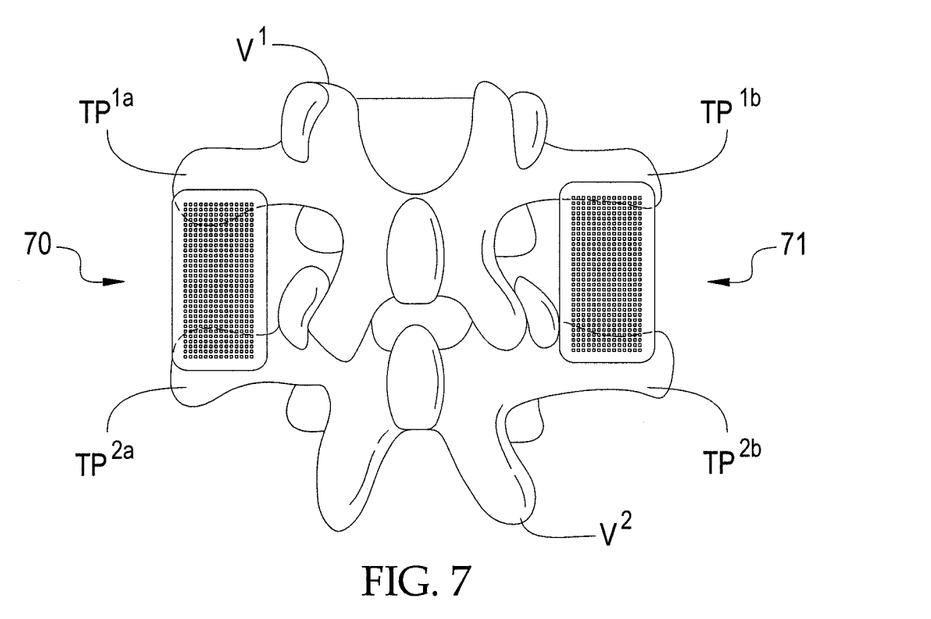
FIG. 7 is a top plan view of a posterolateral spinal fusion implant prepared in vivo in accordance with a preferred embodiment of invention.
Figure 8:
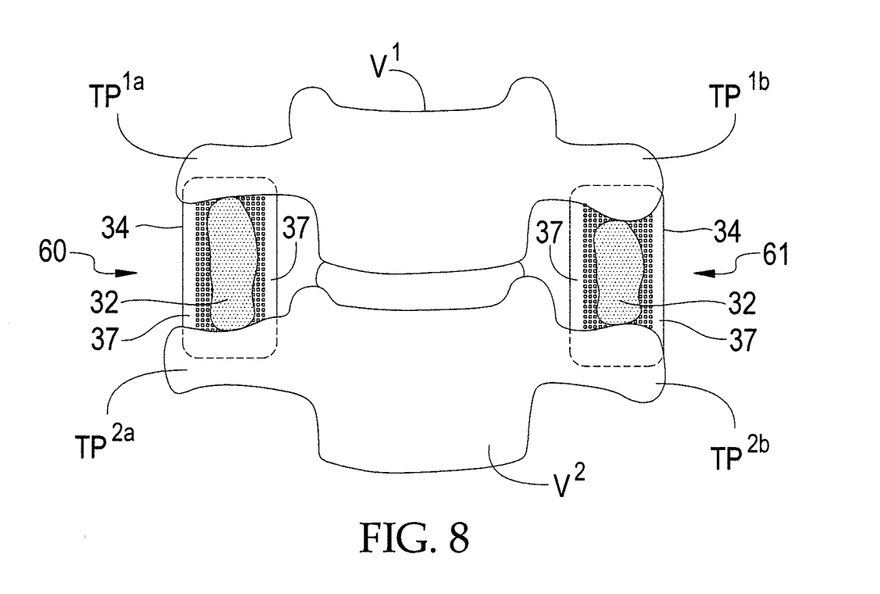
FIG. 8 is a bottom plan view of the implant of FIG. 7.

Referring to FIGS. 7 through 10 are osteoconductive implants according to two more embodiments of the present invention wherein the implants are formed in vivo. In particular, FIGS. 7 and 8 depict implants 70 and 72 that are prepared by inserting or depositing osteoconductive material 32 between a first vertebra $V^1$ and a second vertebra $V^2$ followed by placing a placental membrane sheet on top of or over osteoconductive material 32. In such a procedure, osteoconductive material 32 is deposited in a substantially linear fashion in the space between a transverse process $TP^{1a}$ of $V^1$ and transverse process $TP^{2a}$ of $V^2$. A similar arrangement is shown on the opposite side wherein osteoconductive material 32 contacts transverse process TP$^{1b}$ of the V$^1$ and transverse process TP$^{2b}$ of vertebrae V$^2$ and traverses the space therebetween. With the osteoconductive material deposited between the transverse processes, a placental membrane sheet 34 is laid on top of each of osteoconductive materials 32 so that a first placental membrane sheet 34 traverses the space between transverse process TP$^{1a}$ of V$^1$ and transverse process TP$^{2a}$ of V$^2$ and a second placental membrane sheet 32 traverses the space between transverse process TP$^{1b}$ of the V$^1$ and transverse process TP$^{2b}$ of vertebrae V$^2$. In this embodiment, muscle lying anterior to vertebrae V$^1$ and V$^2$ prevents or inhibits the anterior migration of osteoconductive material 32 from between the transverse processes of the vertebrae. Lateral migration of osteoconductive material 32 is prevented or inhibited by the interaction and contact between the respective peripheries 37 of the placental membrane sheets with the underlying muscle.

Figure 9:
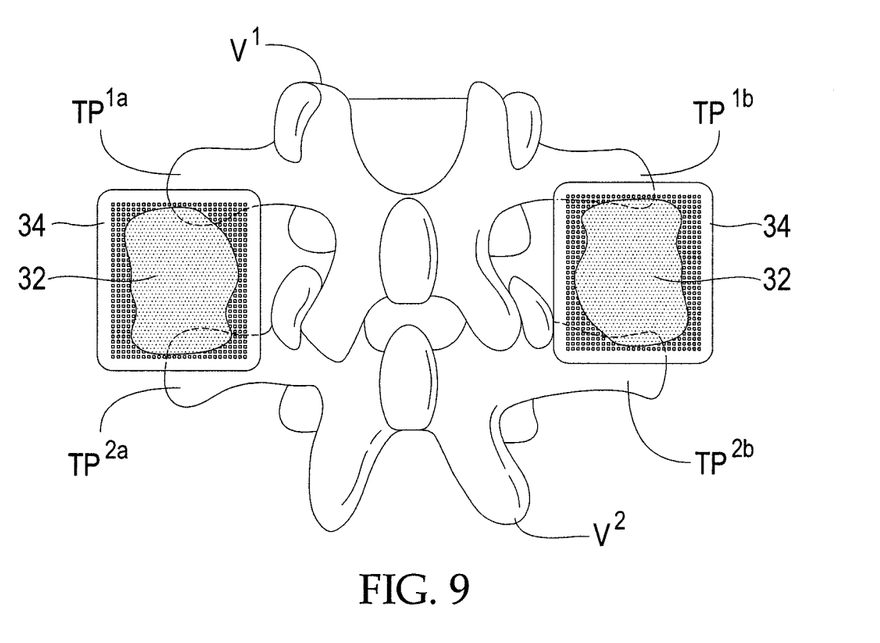
FIG. 9 is a top plan view of a posterolateral spinal fusion implant in an intermediate stage of in vivo preparation in accordance with a preferred embodiment of invention.
Figure 10:
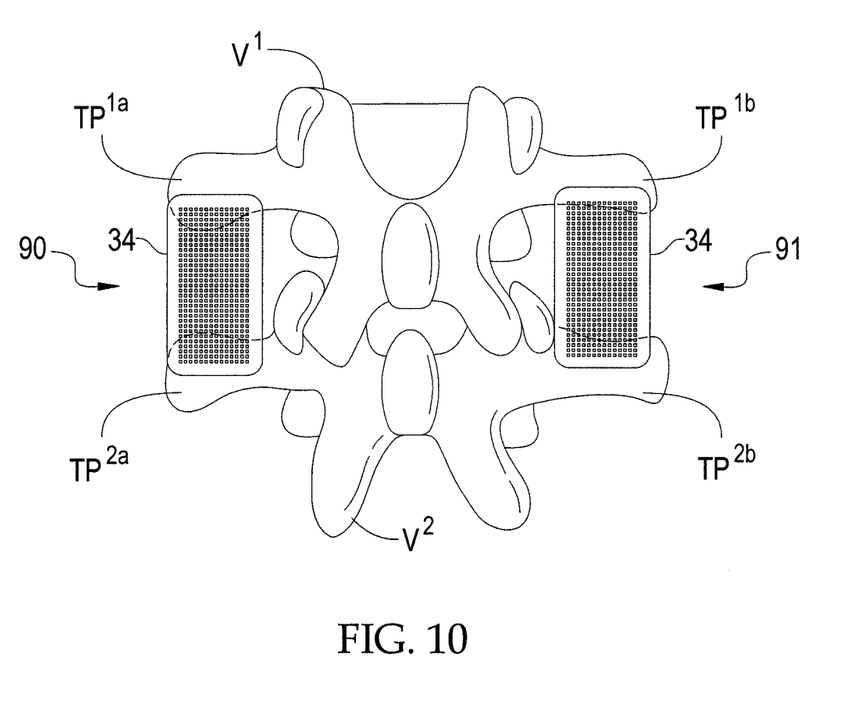
FIG. 10 is a top plan view of the implant of FIG. 9 completed in vivo.

Referring to FIGS. 9 and 10, implants 90 and 91 are prepared by arranging a first placental membrane sheet 34 to traverse the space between a transverse process TP$^{1a}$ of a vertebra V$^1$ and a transverse process TP$^{2a}$ of a vertebra V$^2$ and a second placental membrane sheet 32 to traverse the space between a transverse process TP$^{1b}$ of vertebra V$^1$ and a transverse process TP$^{2b}$ of vertebra V$^2$. Thereafter, a substantially linear line of osteoconductive material 32 is deposited along each of first and second placental membrane sheets 34. Each of the sheets is then folded to entirely encapsulate the osteoconductive material therein. A sectional view of the resulting implants is shown at FIG. 5.

To enhance communication between bones to be fused and the osteoconductive material contained within or covered by placental membrane sheets 34 of any of the implant described above, the sizes of the perforations in the above described implants can be increased by expanding or stretching the placental membrane sheet prior to or subsequent to implantation. The optimal sizing of the openings is primarily a function of the sizes of the osteoconductive materials contained within the implant, and particularly, the smallest of the particulates contained in the osteoconductive material. For example, when bone chips are used, the perforations shall be larger than the perforations used when the osteoconductive materials are granules or powders such a demineralized bone powder.

The present invention is further directed to a kit for promoting bone growth in patients. The kit may include an osteoconductive material, a perforated placental membrane sheet, and optionally, an osteoconductive protein. Each of the components of the kit may be provided in a lyophilized or otherwise dry state, or in a wet state. The kit may also include a structural element in which the components are stably held spaced from one another, in a sterile, medically acceptable packaging system. Additionally, the kit may include instructions for use of the kit components for promoting bone growth within a patient, for example, a spinal fusion procedure such as a posterolateral spinal fusion. Kits of the invention can thus also include other components such as syringes, vials, surgical instruments for minimally invasive or open techniques, spinal rods, spinal cages or other load-bearing interbody fusion devices, spinal plates, bone screws, and the like.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A method for inducing bone growth in a patient comprising:
   providing an implant, wherein the implant includes an osteogenic material in contact with a placental membrane sheet, the placental membrane sheet having an epithelial cell layer, and
   inserting the implant into a patient such that the implant contacts a first bone surface and a second bone surface of the patient so as to induce bone growth there between thereby fusing the first bone surface to the second bone surface,
   and
   wherein the implant is arranged such that epithelial cell layer of the placental membrane sheet is in direct contact with the first bone surface and the second bone surface.

2. The method according to claim 1 wherein the placental membrane sheet is perforated.

3. The method according to claim 2 wherein the site is in a spine or a long bone of the patient.

4. The method according to claim 2 wherein the placental membrane sheet is wrapped around the osteogenic material.

5. The method according to claim 2 wherein the osteogenic material is selected from a group consisting of bone, bone chips, demineralized bone powder, cancellous bone, cortical bone and combinations thereof.

6. The method according to claim 5 further comprising enlarging perforations in the placental membrane sheet by expanding the placental membrane sheet.

7. The method according to claim 6 wherein the perforations are enlarged to desired sizes based upon the osteogenic material that is selected.

8. The method according to claim 2 further comprising fusing the first bone surface to the second bone surface via bone growth through the osteogenic material and the perforations.

9. The method according to claim 1 wherein the first bone surface is a first transverse process in the patient and the second bone surface is a second transverse process in the patient.

10. The method of claim 9 which is a method for posterolateral spinal fusion.

11. The method according to claim 1 wherein the placental membrane sheet includes perforations in a first portion thereof where the implant contacts the first bone surface and in a second portion thereof where the implant contacts the second bone surface.

12. The method according to claim 1 wherein the epithelial cell layer includes a plurality of sessile epithelial cells that are native to the placental membrane sheet.

13. A method for inducing bone growth in a patient comprising:
   wrapping a placental membrane sheet entirely around an osteogenic material to form an implant,
   inserting the implant into a patient such that the implant contacts a first bone surface and a second bone surface of the patient so as to induce bone growth there between thereby fusing the first bone surface to the second bone surface,
   wherein the implant includes perforations through which the osteogenic material communicates with the first bone surface and the second bone surface, and
   wherein the first bone surface is a first transverse process in the patient and the second bone surface is a second transverse process in the patient.

14. The method of claim 13 which is a method for posterolateral spinal fusion.

15. The method according to claim 13 wherein the placental membrane sheet has an epithelial cell layer, and the implant is arranged such that the epithelial cell layer directly contacts the first bone surface and the second bone surface.

16. The method according to claim 13 further comprising selecting the osteogenic material from a group consisting of bone, bone chips, demineralized bone powder, cancellous bone, cortical bone and combinations thereof.

17. The method according to claim 16 further comprising enlarging the perforations to thereby improve communication between the osteogenic material and the first bone surface and the second bone surface.

18. The method according to claim 13 wherein the epithelial cell layer includes a plurality of sessile epithelial cells that are native to the placental membrane sheet.

19. A method for inducing bone growth in a patient comprising:
placing an osteogenic material and a placental membrane sheet into a patient at a site between a first bone surface and a second bone surface, wherein the placental membrane sheet has an epithelial cell layer, so as to induce bone growth there between and thereby fuse the first bone surface with the second bone surface, and
folding the placental membrane sheet over the osteogenic material
such that the epithelial cell layer of the placental membrane sheet faces away from the osteogenic material,
wherein the method is a posterolateral spinal fusion method.

20. The method according to claim 19 further comprising perforating the placental membrane sheet.

21. The method according to claim 20 wherein the method comprises placing the placental membrane sheet at the site after placement of the osteogenic material.

22. The method according to claim 20 further comprising expanding the placental membrane sheet thereby increasing sizes of perforations in the placental membrane sheet.

23. The method according to claim 19 wherein the folding step results in the placental membrane sheet being present on top of the osteogenic material.

24. The method according to claim 19 further comprising extending the placental membrane sheet to and between the first bone surface and the second bone surface.

25. The method according to claim 19 wherein the method comprises placing the placental membrane sheet at the site prior to placement of the osteogenic material.

26. The method according to claim 25 wherein the osteogenic material is placed on top of the placental membrane sheet and the placental sheet is folded over the osteogenic material.

27. The method according to claim 19 further comprising selecting the osteogenic material from a group consisting of bone, bone chips, demineralized bone powder, cancellous bone, cortical bone and combinations thereof.

28. The method according to claim 19 wherein the epithelial cell layer includes a plurality of sessile epithelial cells that are native to the placental membrane sheet.

29. A method for inducing bone growth in a patient comprising:
placing an osteogenic material and a placental membrane sheet into a patient at a site between a first bone surface and a second bone surface, wherein the placental membrane sheet has an epithelial cell layer, so as to induce bone growth there between and thereby fuse the first bone surface with the second bone surface,
extending the placental membrane sheet to and between the first bone surface and the second bond surface, and
arranging the placental membrane sheet so that the epithelial cell layer of the placental membrane sheet faces away from the osteogenic material,
wherein the first bone surface is a first transverse process in the patient and the second bone surface is a second transverse process in the patient.

30. A method for inducing bone growth in a patient comprising:
placing an osteogenic material and a placental membrane sheet into a patient at a site between a first bone surface and a second bone surface, wherein the placental membrane sheet has an epithelial cell layer, so as to induce bone growth there between and thereby fuse the first bone surface with the second bone surface, and
arranging the placental membrane sheet so that the epithelial cell layer of the placental membrane sheet faces away from the osteogenic material,
wherein the osteogenic material is selected from the group consisting of bone, bone chips, demineralized bone powder, cancellous bone, cortical bone and combinations thereof, and
wherein the first bone surface is a first transverse process in the patient and the second bone surface is a second transverse process in the patient,
wherein the osteogenic material is deposited in a line to and between a first transverse process in the patient and a second transverse process in the patient, and
wherein the line of osteogenic material is at least partially covered by the placental membrane sheet.

31. A method for inducing bone growth in a patient comprising:
placing an osteogenic material and a placental membrane sheet into a patient at a site between a first bone surface and a second bone surface, wherein the placental membrane sheet has an epithelial cell layer, so as to induce bone growth there between and thereby fuse the first bone surface with the second bone surface, and
arranging the placental membrane sheet so that the epithelial cell layer of the placental membrane sheet faces away from the osteogenic material,
wherein the placental membrane sheet and the osteogenic material are formed into an elongate implant having a first perforated end, an opposing second perforated end and a non-perforated midsection.

* * * * *